United States Patent
Chacon Quiros et al.

(10) Patent No.: US 10,905,466 B2
(45) Date of Patent: Feb. 2, 2021

(54) APPARATUSES FOR THE IMPLANTATION OF MEDICAL DEVICES AND METHODS OF USE THEREOF

(71) Applicant: Establishment Labs S.A., Alajuela (CR)

(72) Inventors: Juan Jose Chacon Quiros, Alajuela (CR); Rudy A. Mazzocchi, New York, NY (US); Roberto De Mezerville, Alajuela (CR); John Hancock, Santa Barbara, CA (US); Nathalia Araujo, Alajuela (CR); Matthew Solar, Melbourne, FL (US); Nicholas Lewin, New York, NY (US)

(73) Assignee: Establishment Labs S.A., Alajuela (CR)

( * ) Notice: Subject to any disclaimer, the term of this patent is extended or adjusted under 35 U.S.C. 154(b) by 154 days.

(21) Appl. No.: 16/092,878

(22) PCT Filed: Apr. 14, 2017

(86) PCT No.: PCT/US2017/027807
§ 371 (c)(1),
(2) Date: Oct. 11, 2018

(87) PCT Pub. No.: WO2017/181144
PCT Pub. Date: Oct. 19, 2017

(65) Prior Publication Data
US 2019/0125401 A1  May 2, 2019

Related U.S. Application Data

(60) Provisional application No. 62/393,970, filed on Sep. 13, 2016, provisional application No. 62/323,160, filed on Apr. 15, 2016.

(51) Int. Cl.
*A61F 2/12* (2006.01)
*A61B 17/34* (2006.01)
(Continued)

(52) U.S. Cl.
CPC ........ *A61B 17/3468* (2013.01); *A61F 2/0095* (2013.01); *A61F 2/12* (2013.01);
(Continued)

(58) Field of Classification Search
CPC ............................ A61F 2/12; A61B 17/3468
(Continued)

(56) References Cited

U.S. PATENT DOCUMENTS

| | | |
|---|---|---|
| 3,815,476 A | 6/1974 | Green et al. |
| 5,500,019 A * | 3/1996 | Johnson ........... A61B 17/00234 |
| | | 128/898 |

(Continued)

FOREIGN PATENT DOCUMENTS

| | | | |
|---|---|---|---|
| CN | 201551714 U | 8/2010 | |
| CN | 105105868 A | 12/2015 | |
| WO | WO-2020070676 A1 * | 4/2020 | ......... A61B 17/3468 |

OTHER PUBLICATIONS

International Search Report for PCT/US2017/027807 dated Oct. 10, 2017 (published as WO 2017/181144 A3 dated Oct. 19, 2017) (6 pages).

*Primary Examiner* — Suzette J Gherbi
(74) *Attorney, Agent, or Firm* — Bookoff McAndrews, PLLC

(57) ABSTRACT

A medical device may include a shaft extending between a proximal end and a distal end. The shaft may include a lumen therein. The medical device may include a handle coupled to the proximal end of the shaft and may include a mode selector. The mode selector may be adapted to transition between a first mode and a second mode of the (Continued)

medical device. The medical device may further include a compressed fluid source. In the first mode, the compressed fluid source may be fluidly coupled with the shaft so as to impart a negative pressure in at least a portion of the lumen. In the second mode, the compressed fluid source may be fluidly coupled with the shaft so as to impart a positive pressure in the at least a portion of the lumen.

11 Claims, 9 Drawing Sheets

(51) Int. Cl.
*A61F 2/00* (2006.01)
*A61M 5/20* (2006.01)
*A61M 5/31* (2006.01)
*A61B 17/00* (2006.01)
*A61B 90/00* (2016.01)

(52) U.S. Cl.
CPC ... *A61M 5/2053* (2013.01); *A61B 2017/0023* (2013.01); *A61B 2017/0042* (2013.01); *A61B 2017/00544* (2013.01); *A61B 2017/00548* (2013.01); *A61B 2017/00792* (2013.01); *A61B 2017/00796* (2013.01); *A61B 2090/037* (2016.02); *A61F 2250/009* (2013.01); *A61F 2250/0071* (2013.01); *A61M 2005/3128* (2013.01); *A61M 2210/1007* (2013.01)

(58) Field of Classification Search
USPC .......................................................... 623/7–8
See application file for complete search history.

(56) References Cited

U.S. PATENT DOCUMENTS

| | | |
|---|---|---|
| 5,571,178 A | 11/1996 | Ledergerber |
| 10,398,543 B1 | 9/2019 | Solar et al. |
| 2005/0049701 A1 | 3/2005 | Brennan |
| 2006/0224144 A1 | 10/2006 | Lee |
| 2009/0177165 A1 | 7/2009 | Tsao |
| 2009/0287190 A1 | 11/2009 | Shippert |
| 2012/0083768 A1* | 4/2012 | Skora ..................... A61B 46/10 606/1 |
| 2013/0304051 A1 | 11/2013 | Kimmel et al. |
| 2014/0200511 A1* | 7/2014 | Boyden ................ A61K 9/1641 604/67 |
| 2014/0358155 A1 | 12/2014 | DeBoer et al. |
| 2016/0100958 A1* | 4/2016 | Behzadi ................ A61F 2/4609 606/91 |
| 2018/0014900 A1* | 1/2018 | Vayser ..................... A61B 1/06 |
| 2020/0046342 A1* | 2/2020 | Hess .................. A61B 17/3421 |
| 2020/0155313 A1* | 5/2020 | Zhang ................... A61F 2/2457 |
| 2020/0163543 A1* | 5/2020 | Schutt ................ A61B 17/7065 |

* cited by examiner

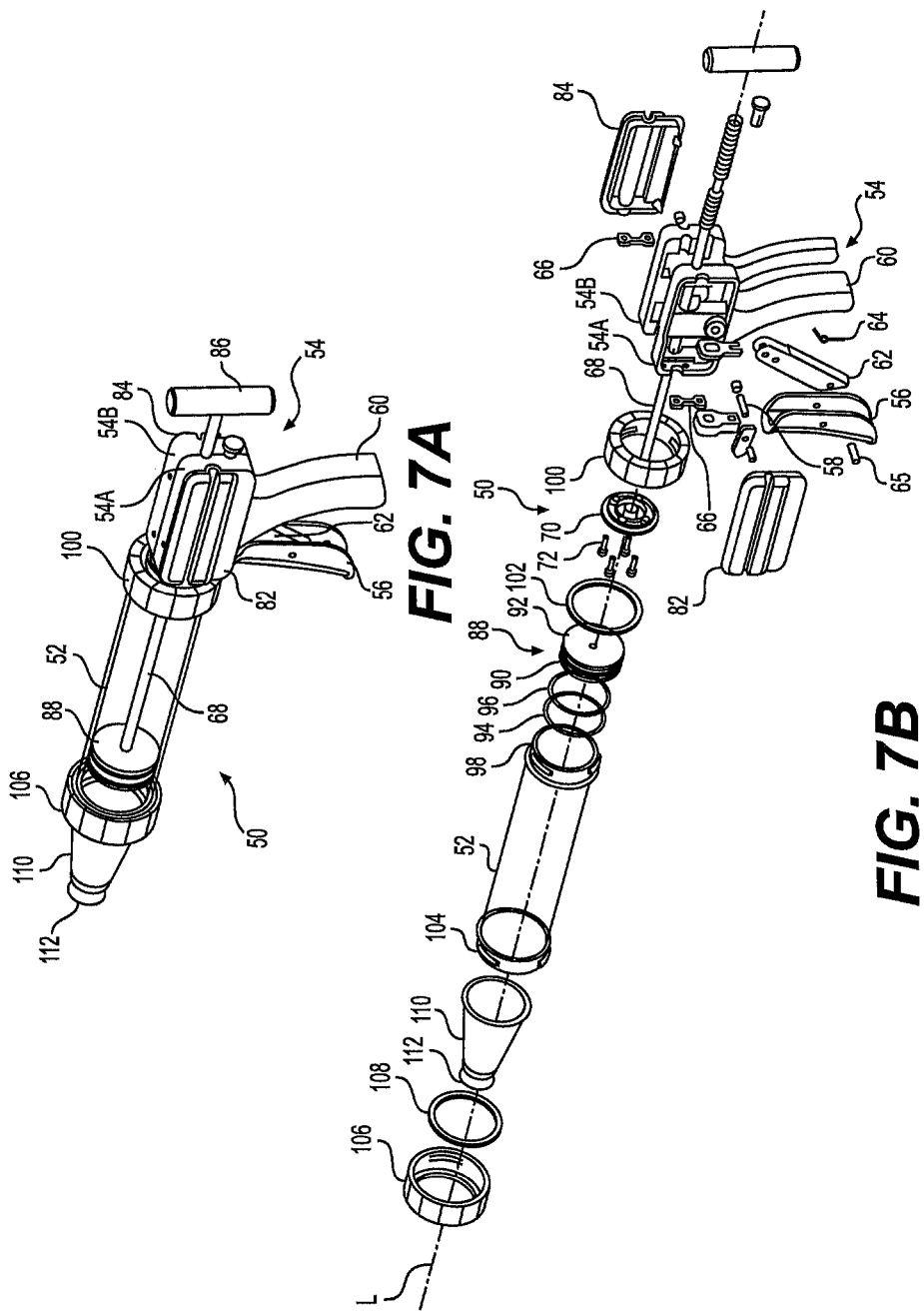

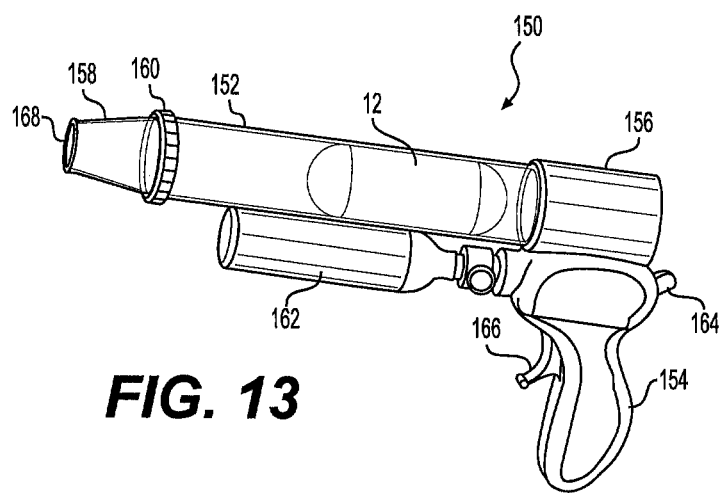
FIG. 13
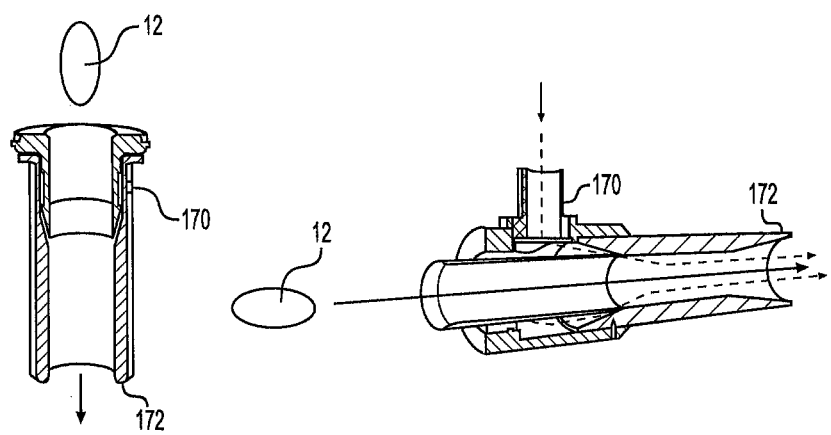
FIG. 14
FIG. 15

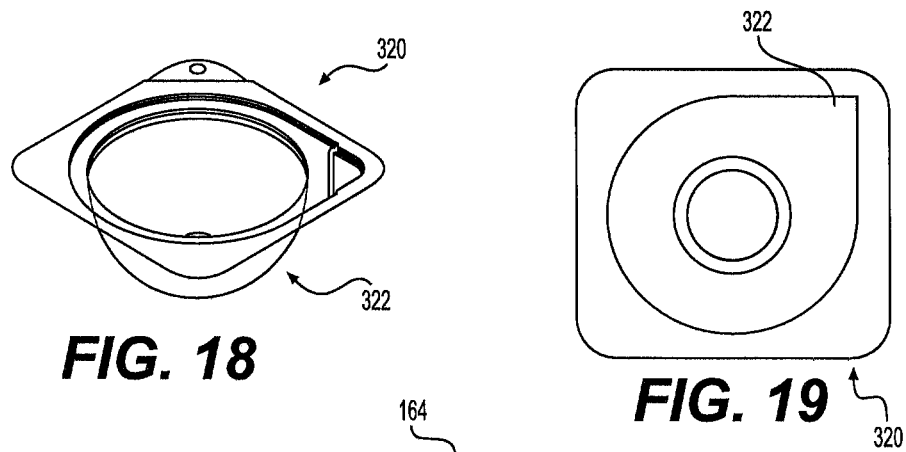
FIG. 18
FIG. 19
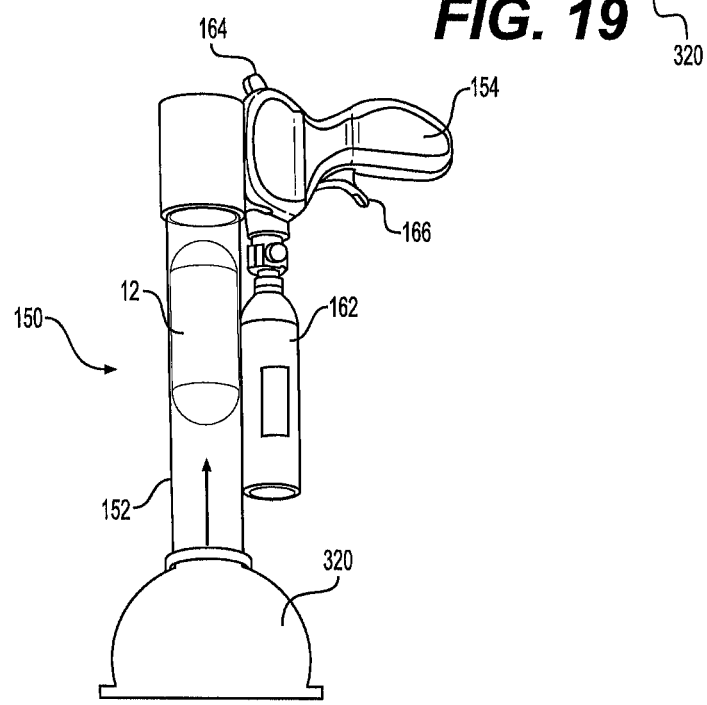
FIG. 20

APPARATUSES FOR THE IMPLANTATION OF MEDICAL DEVICES AND METHODS OF USE THEREOF

CROSS-REFERENCE TO RELATED APPLICATIONS

This patent application is a U.S. national stage filing under 35 U.S.C. § 371 of International Application No. PCT/US2017/027807, filed on Apr. 14, 2017, which claims the benefit of priority under 35 U.S.C. § 119 of U.S. Provisional Patent Application No. 62/323,160, filed on Apr. 15, 2016, and U.S. Provisional Patent Application No. 62/393,970, filed on Sep. 13, 2016, the entirety of each of which is herein incorporated by reference.

TECHNICAL FIELD

Aspects of the present disclosure generally relate to medical devices and procedures. In particular, some aspects relate to minimally invasive apparatuses for the implantation of medical devices and methods related thereto.

BACKGROUND

Breast implants are among the largest implantable medical devices in the human body today. Due to their volume, mass, and surface area, implantation of these devices can require larger incisions for insertion and proper positioning. Current techniques often create extensive surgical wounds that can stimulate a complex and dynamic healing process, e.g., to replace devitalized and missing cellular structures and tissue layers. For example, many current techniques require a large incision, manipulated by retractors and tissue-spreaders to expand and hold open the incision site for the physical manipulation of the implant into the tissue pocket. These techniques can increase the size of the scar, the probability of damage to the implant, and/or the possibility of infection; can require insertion of drainage tubes to evacuate serous fluids from surrounding tissue and capillary damage; and/or can accelerate inflammatory responses that impact the healing process. In addition, keloids and hypertrophic scars represent an overgrowth of dense fibrous tissue that usually develops after healing of a skin injury. It is recognized that the larger the incision, the greater potential incidence for keloid and hypertrophic scarring. Certain patients are also more susceptible to, and are at higher risk of, keloid formation.

The systems, devices, and methods of the current disclosure may rectify or lessen some or all of the challenges described above, and/or may address other needs not met by prior technology.

SUMMARY

Aspects of the present disclosure relate to, among other things, minimally invasive devices for the implantation of medical devices and methods related thereto. Each of the aspects disclosed herein may include one or more of the features described in connection with any of the other disclosed aspects.

In one aspect, a medical device may include a shaft extending between a proximal end and a distal end. The shaft may include a lumen therein. A handle may be coupled to the proximal end of the shaft and may include a mode selector. The mode selector may be adapted to transition between a first mode and a second mode of the medical device. The medical device may further include a compressed fluid source. In the first mode, the compressed fluid source may be fluidly coupled with the shaft so as to impart a negative pressure in at least a portion of the lumen. In the second mode, the compressed fluid source may be fluidly coupled with the shaft so as to impart a positive pressure in the at least a portion of the lumen.

Examples of the medical device may further include any one or more of the following features. A nozzle may be coupled to the distal end of the shaft. The nozzle may be tapered towards a distal opening. The distal opening of the nozzle may be ovular. The nozzle may be removably coupled to the distal end of the shaft. The compressed gas source may include a cartridge coupled to, and detachable from, the handle. A pump may be fluidly coupled to the compressed gas source. The compressed gas source may include a tubing assembly. The medical device may include a valve mechanism.

In another aspect, a medical device may include a shaft extending between a proximal end and a distal end. The shaft may include a lumen therein. A handle may be coupled to the shaft. The handle may comprise a mode selector and an actuator. The mode selector may be adapted to transition between a first mode or a second mode of the medical device. A valve mechanism may be in communication with the mode selector and the actuator. A compressed fluid source may be coupled to the shaft. In the first mode, the compressed fluid source may impart a negative pressure controlled by the actuator in at least a portion of the lumen. In the second mode, the compressed fluid source may impart a positive pressure controlled by the actuator in the at least a portion of the lumen.

Examples of the medical device may further include any one or more of the following features. The compressed gas source may include a cartridge coupled to the handle and may be removable from the medical device via mating features. A pump may be fluidly coupled to the compressed gas source and housed within the handle. The compressed gas source may include a tubing assembly adapted for attachment to a centralized gas supply. A nozzle may be removably attached to the distal end of the shaft. The nozzle may be tapered and include a distal opening.

In a further aspect, a method may include selecting a first mode of a medical device via a mode selector coupled to a handle of the medical device. The medical device may further include a shaft including a lumen. The method also may include applying vacuum pressure to the lumen via an actuator coupled to the handle to draw an implant into the lumen. Further, the method may include selecting a second mode of the medical device via the mode selector applying expulsion pressure to the lumen via the actuator to expel the implant from the shaft.

Examples of the method may further include any one or more of the following features. The method may include coupling a nozzle to a distal end of the shaft after applying the vacuum pressure and before applying the expulsion pressure. The medical device may include or may be coupled to a source of compressed gas for applying the vacuum pressure and the expulsion pressure. The implant may be a breast implant, and drawing the implant into the lumen may compress the breast implant. The method may include coupling a distal end of the shaft to a sterile package containing the implant before applying the vacuum pressure.

In a further aspect, a medical device may include a shaft extending between a proximal end and a distal end. The shaft may include a lumen therein. A handle may be coupled to the proximal end of the shaft. A valve assembly may be disposed within the handle. A tubing assembly may have a first end coupled to the handle and a second end adapted for attachment to a centralized gas supply.

Examples of the medical device may further include any one or more of the following features. A nozzle may be removably attached to the distal end of the shaft. The nozzle may be tapered and include a distal opening. The distal opening of the nozzle may be ovular.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary aspects that, together with the written description, serve to explain the principles of this disclosure.

FIGS. 7A and 7B illustrate an additional exemplary introducer device, according to aspects of the present disclosure;

FIG. 13 illustrates another exemplary introducer device, according to aspects of the present disclosure;

FIGS. 14 and 15 illustrate fluid flow through an exemplary introducer device, according to aspects of the present disclosure;

FIGS. 18 and 19 illustrate a sterile package of an exemplary implant; and

FIG. 20 illustrates an exemplary introducer device coupled to the sterile package of FIGS. 18 and 19.

DETAILED DESCRIPTION

Examples of the present disclosure relate to systems, devices, and methods for treating internal areas of a patient's body. Such systems or devices may include an introducer device and an implant for introduction into the body (e.g., into a breast pocket) of a patient. Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative and directional positions of the components of an exemplary introducer device. When used herein, "proximal" refers to a position closer to the exterior of the body of the patient or closer to an operator and/or medical professional using introducer device. In contrast, "distal" refers to a position further away from the operator and/or medical professional using the introducer device, or closer to the interior of the body of the patient.

The introducer devices described herein may be used to deliver any one or more implants via any one or more of various minimally invasive procedures. In at least one example, the implant may be a breast implant with elastic properties, e.g., super visco-elastic and/or highly elastic properties. According to some aspects of the present disclosure, the implant may comprise silicone filling gel (e.g., the breast implant may be pre-filled with the silicone gel prior to implantation). The silicone filling gel may have a penetration value ranging from 1.0-6.0. The penetration value is a factor that measures the firmness of a colloid, such as a silicone gel. The implant may comprise a shell (e.g., an outer casing) with biocompatible surfaces. In some aspects, the shell may have a combination of low roughness, high kurtosis (e.g., referring to the distribution of peak heights and valley depths of the surface), and skewness of the surface. Any of the features of implants disclosed in U.S. Provisional Application No. 62/334,667, filed on May 11, 2016, and/or U.S. Provisional Application No. 62/410,121, filed on Oct. 19, 2016, are incorporated by reference herein in their entireties. As such, the shell may have friction surface properties to facilitate smooth delivery and implantation of the implant within the body of the patient. Examples of suitable breast implants may include, but are not limited to, Motiva implants produced by Establishment Labs, such as, e.g., Motiva Implant Matrix® SilkSurface™ and VelvetSurface™. While references to breast implants are used throughout the remainder of this disclosure, the disclosure is not so limited. Rather, the systems, devices, and methods disclosed herein may be used to deliver any one or more of breast, gluteal, calf, and/or other such implants into the body of the patient.

Figure 1:
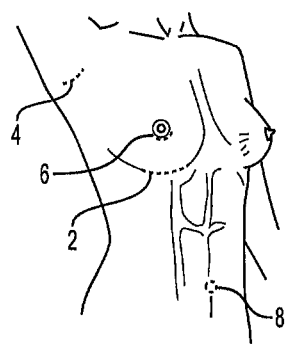
FIG. 1 illustrates a variety of incision locations for implantation of a breast implant.
Figure 8A:
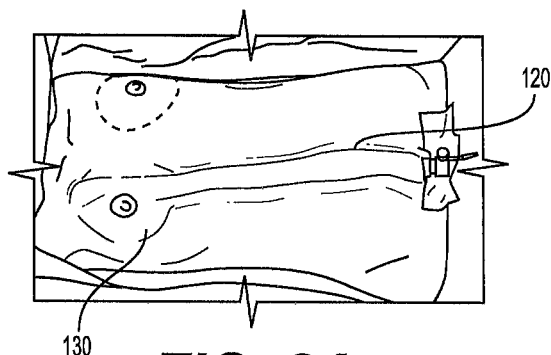
FIGS. 8A and 8B depict the formation of a subcutaneous tunnel during a procedure.

FIG. 1 illustrates a variety of incision locations for implantation of a breast implant. As shown, a breast implant may be introduced into a breast pocket (e.g., breast pocket 130, FIG. 8A) of a patient through an under-the-breast or inframammary incision 2; a transaxillar or through-the-armpit incision 4; the periareolar or areolar incision 6; or the transumbilical or through-the-belly-button incision 8. As shown, the various incision types may necessitate an opening of varying size and/or dimension. For example, the size of an inframammary incision 2 is typically larger than a transumbilical incision 8. The selection of an incision type (e.g., insertion site) and size may depend on a number of variables and patient/physician preferences such as, e.g., the size and/or shape of the implant, the physical characteristics of the patient (e.g., the amount of adipose tissue, degree of skin elasticity, and/or physical condition of the patient), the patient's age, and/or the patient's lifestyle.

Figure 2:
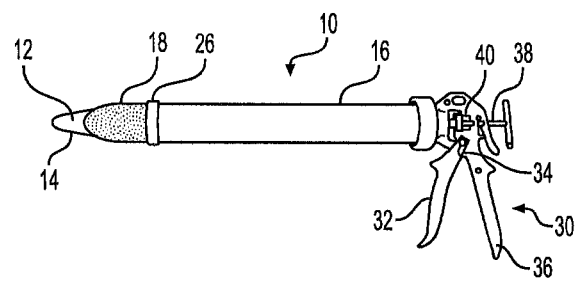
FIG. 2 illustrates an exemplary introducer device, according to aspects of the present disclosure.

Disclosed herein are a variety of instruments, devices (e.g., introducer devices), systems, and methods to allow for the introduction of an elastomeric implant (such as, e.g., breast, gluteal, and/or calf implants) in a minimally-invasive manner. FIG. 2 illustrates an exemplary introducer device 10 for delivery of an implant 12. Implant 12 may comprise a high strength shell 14 with visco-elastic and low friction surface properties as discussed above. Implant 12 is moldable, pliant, compressible, or otherwise movable between a compressed, elongated, insertion configuration (as shown in e.g., FIGS. 2, 3, and 5A) and a deployed or expanded configuration (as shown in, e.g., FIG. 5B). A maximum diameter or dimension of implant 12 in the insertion configuration may be limited by a size of a lumen of a shaft 16 within which implant 12 may be received. For example, in some examples, the inner diameter of the shaft may range from about 1-3 inches or from about 1.5-2.5 inches, e.g., about 1, 1.5, 2, 2.5, or 3 inches. As shown, the insertion configuration is a low profile or compressed configuration. Implant 12 may be positioned within introducer device 10 in the insertion configuration and, following delivery out of introducer device 10 and into the body of the patient, implant 12 may expand, decompress, or otherwise assume the deployed configuration.

As shown in FIG. 2, introducer device 10 includes a shaft 16 having a lumen (not shown in the orientation of FIG. 2) therein. As mentioned above, the inner diameter of the shaft 16 may range from about 1-3 inches or from about 1.5-2.5 inches, e.g., about 1, 1.5, 2, 2.5, or 3 inches. Further, for example, the outer diameter of the shaft 16 may range from about 1.05 inches to about 3.5 inches, e.g., about 1.05, 1.55, 2.05, 2.55, or 3.05 inches. The length of the shaft 16 may range from about 7 inches to about 12 inches, or from about 8 inches to about 10 inches, e.g., a length of about 7, 7.5, 8, 8.5, 9, 9.5, 10, 10.5, 11, 11.5, or 12 inches. The dimensions of the shaft 16 may be selected or correspond to the volume of the implant 12. In at least one example, an introducer device 10 having a 9-inch shaft may be used for a 300 cc implant. Further, for example, a 1-inch shaft may be used for a 200 cc implant, or a shaft between about 2-3 inches may be used for an implant of 500 cc or more. Any one or more portions of shaft 16, such as an inner surface of shaft 16 may include a lubricious (e.g., hydrophilic) coating to reduce the coefficient of friction between one or more portions (e.g., the inner surface) of introducer device 10 and one or more portions (e.g., shell 14) of implant 12. For example, prior to implantation, implant 12 may be housed, received, or otherwise at least partially disposed within the lumen of shaft 16 of introducer device 10. The hydrophilic coating may reduce the coefficient of friction between shell 14 and the interior surface of shaft 16, enabling a smooth transition between the insertion configuration and the deployed configuration, e.g., upon exit of implant 12 from introducer device 10.

Optionally, introducer device 10 may include a unique device identifier (UDI) with information useful for identifying introducer device 10. For example, the UDI may include a micro-transponder for post-implantation device recognition and traceability. In some aspects, the micro-transponder includes one or more sensors with the ability to measure temperature, change in electrical impedance, and/or pressure, e.g., to be used as a control signal to alert or diagnose shell 14 rupture, infection of the patient's tissue, and/or signs of an inflammatory response of the patient's tissue by monitoring the surrounding tissue temperature. Such a UDI/sensor may be placed in any suitable position on or within introducer device 10, including, for example, the inner surface of the introducer device 10 proximate and/or in contact with implant 12.

Figure 3:
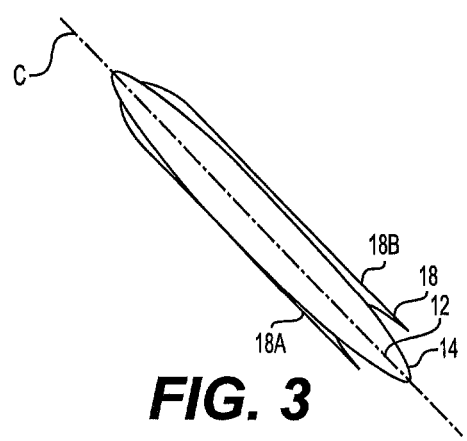
FIG. 3 illustrates an exemplary chamber of the introducer device of FIG. 2, according to aspects of the present disclosure.
Figure 4A:
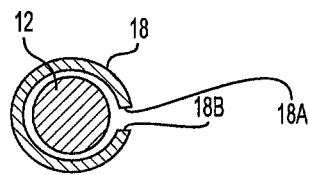
FIGS. 4A and 4B illustrate additional exemplary chambers of the introducer device of FIG. 2, according to further aspects of the present disclosure.
Figure 4B:
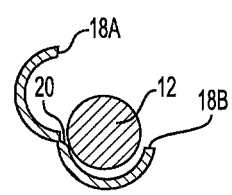

In some aspects, implant 12 may be pre-loaded or inserted into a chamber (or introducer sheath) 18 to facilitate the sterile loading of implant 12 into shaft 16 and/or manipulate (e.g., compress, elongate, etc.) implant 12 toward the insertion configuration. Additionally, chamber 18 (or chamber 22 of FIGS. 5A and 5B, described below) may protect implant 12 during an implantation procedure. For example, introducer device 10 may provide for an implant profile diameter that correlates to a small incision in the range of about 1.0 cm to less than about 3.0 cm, or in the range of about 2.0 cm to 2.5 cm. As such, chamber 18 may compress the diameter of implant 12 equal to or smaller than the incision size. Chamber 18 may have any appropriate shape or arrangement to urge implant 12 toward and/or maintain implant 12 in the insertion configuration while inside introducer device 10. As shown in FIGS. 2 and 3, for example, chamber 18 is a foldable or rollable, highly-flexible, thin polymeric sheathing material that may be rolled or wrapped at least partially around implant 12 to thereby compress and/or elongate implant 12 into the insertion configuration. Once wrapped around implant 12, chamber 18 may have a U-shaped cross-section as shown in FIG. 3. Alternatively, once wrapped around implant 12, chamber 18 may have a C-shaped shaped cross-section, as shown in FIG. 4A. While each of FIGS. 3 and 4A illustrate a gap or space between terminating edges 18A and 18B of chamber 18, the disclosure is not so limited. In some arrangements, edges 18A and 18B may abut or overlap one another such that the chamber 18 envelopes or surrounds the entire circumferential surface of implant 12 in the insertion configuration. Optionally, chamber 18 may include a hinge 20 between portions of chamber 18, e.g., providing a generally clam-shell (e.g., two-part, halved) arrangement. Hinge 20 may be located along an internal or external surface of chamber 18. In some examples, hinge 20 may be a living hinge (e.g., a hinge formed of a thinned dimension relative to a remainder of chamber 18 so as to enable bending along the thinned portion). In any such manner, hinge 20 is positioned so as to minimize exposure of hinge 20 to implant 12 and/or surrounding patient tissue, thereby preventing inadvertent trauma, injury, or abrasion of implant 12 and/or patient tissue.

Figure 5A:
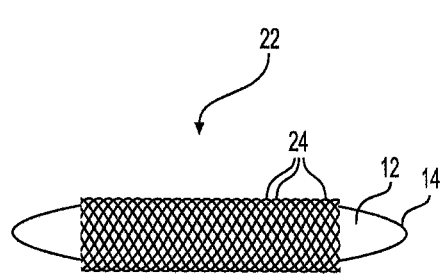
FIGS. 5A and 5B illustrate further exemplary chambers of the introducer device of FIG. 2, according to aspects of the present disclosure.
Figure 5B:
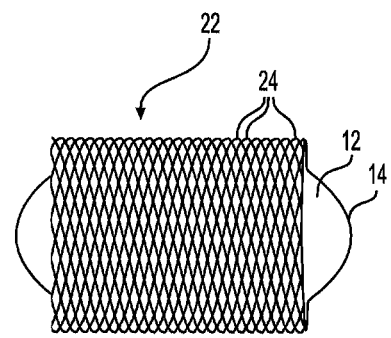

In some arrangements, the chamber may comprise a shape memory material. For example, chamber 18 may be replaced with chamber 22 illustrated in FIGS. 5A and 5B. Chamber 22 includes one or more shape-memory materials. Exemplary shape-memory materials include, but are not limited to, shape memory polymers and metal alloys such as nickel-titanium (Nitinol, including nickel-titanium wire structures) that may have thermal-recovery properties. For example, chamber 22 includes a plurality of struts 24 monolithically formed or woven, braided, or otherwise joined together in an expandable structure. In such an arrangement, chamber 22 may be tubular and allow for the constriction and/or containment of implant 12 within the tubular structure of chamber 22 that incorporates the shape-memory material(s), at a low transition temperature (e.g., lower than ambient room temperature), thereby reducing the insertion diameter of implant 12 to less than or equal to the incision size, as shown in FIG. 5A. Upon warming (e.g., by exposure to body temperature or a warm saline flush), the shape-memory material may expand to a preset or predetermined shape and diameter, as shown in FIG. 5B. Expansion of chamber 22 according to this arrangement may allow for the expansion of implant 12 housed therein, and facilitate removal of the chamber 22.

Returning to FIG. 2, at least a portion (e.g., a proximal end) of chamber 18 (or chamber 22) is received within the lumen of shaft 16 and secured thereto via a connector 26. For example, connector 26 may include a compression ring that tightens circumferentially around chamber 18 (or chamber 22) and around a distal end of shaft 16 to secure chamber 18 (or chamber 22) to shaft 16. In such a manner, connector 26 prevents movement of chamber 18 (or chamber 22) relative to shaft 16.

Once implant 12 is received within shaft 16, e.g., via chamber 18 or chamber 22, a medical professional may grasp a handle 30 of introducer device 10. Handle 30 may be a squeeze-type or compression handle, e.g., operating in a manner similar to a caulking gun, in which a first arm 32 is rotatable about a pivot 34 and movable toward a second arm 36. Pivot 34, in turn, is coupled to a plunger rod 38 via any appropriate gear and/or linkage system (not shown) such that rotational movement of pivot 34 is transferred into linear movement of plunger rod 38. Such a gearing and/or linkage system may include a ratchet 40 to enable controlled, gentle, and incremental advancement of implant 12 via a plunger head (not shown) coupled to a distal end of plunger rod 38. The plunger head may have a dimension (e.g., diameter) corresponding or similar to a dimension (e.g., diameter) of implant 12 in the insertion configuration. As such, upon squeezing first arm 32 toward second arm 36, plunger rod 38 is advanced toward chamber 18 (or chamber 22) and the plunger head forces, pushes, advances, or otherwise moves implant 12 distally of chamber 18 (or chamber 22) (as shown in FIG. 2) and into the breast pocket of a patient (or other site of implantation suitable for the type of implant), while chamber 18 (or chamber 22) remains securely connected to shaft 16 via connector 26.

In another arrangement, however, plunger rod 38 is stationary so as to prevent implant 12 from "backing out" of chamber 18, e.g., during an implantation procedure. For example, the plunger head of plunger rod 38 may be positioned at a proximal end of chamber 18 so as to limit proximal movement of implant 12 (e.g., the plunger head may abut, contact, or otherwise inhibit movement of implant 12 proximally). In such cases, introducer device 10 may include a mechanism for retracting chamber 18 in order to release implant 12 from chamber 18. In at least one example, squeezing first arm 32 toward second arm 36 of handle 30 may pull chamber 18 proximally while plunger rod 38 remains stationary to prevent proximal movement of implant with chamber 18.

Figure 6:
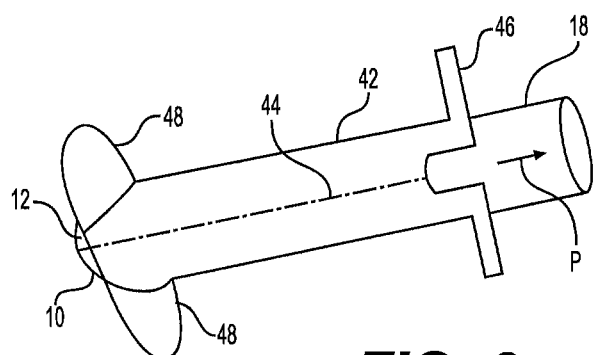
FIG. 6 illustrates an exemplary chamber having a sheath, according to aspects of the present disclosure.

FIG. 6 illustrates another example of retraction of chamber 18, wherein a frangible sheath 42 is positioned about chamber 18, e.g., proximate a distal end of chamber 18. Sheath 42 may comprise a flexible polymeric material and include a perforate line 44 (e.g., a series of small holes or thinned portions extending through at least a portion of the thickness of sheath 42) so as to facilitate tearing along perforate line 44. A proximal end of sheath 42 includes one or more flanges, grips, or tabs 46 to allow for a secure grip on sheath 42 by the medical professional. Optionally, a distal end of sheath 42 includes one or more retractors 48, described in further detail below. In such an arrangement, delivery of implant 12 is performed via proximal retraction of sheath 42 or chamber 18 (or chamber 22) (e.g., in the direction of arrow P), e.g., relative to the plunger head of plunger rod 38 discussed above. To do so, a medical professional may pull on tabs 46 of sheath 42 which tears (e.g., peels away) sheath 42 along perforate line 44 thereby slowly exposing a distal portion of implant 12, allowing the natural expansion of exposed implant 12 (e.g., the exposed gel-filled structure) to pull the remaining portion of implant 12 out of chamber 18 and into the breast pocket (or other site of implantation for the type of implant) of the patient.

As shown in FIG. 6, retractor(s) 48 extend radially outward (e.g., relative to a longitudinal axis C of chamber 18, FIG. 3), and may have the shape of a flange or cone. In some examples, retractor(s) may have a shield-like configuration. In use, retractor(s) 48 may be placed within the incision during an implantation procedure and may help to minimize damage to the skin and/or other tissues of the patient, and/or may help to stabilize the introducer device 10 during the implantation procedure. As shown, retractor(s) 48 are integrated with sheath 42. However, the disclosure is not so limited. In some arrangements, retractor(s) 48 may be separate components used independently of any other device, or, may be coupled to any one or more of chamber 18 (or chamber 22) or shaft 16. In any arrangement, however, retractor(s) 48 may help to minimize the risk of introducing bacteria (or other micro-organisms) into the incision site. Additionally or alternatively, the retractor(s) 48 may serve to minimize the exposure of implant 12 to other surgical instruments (e.g., scalpels, needles, forceps, etc.) to reduce the risk of damage to implant 12 during the implantation procedure. For example, retractor(s) 48 may minimize the risk of rupturing shell 14 of implant 12 during implantation.

Retractor(s) 48 may be flexible or semi-rigid (e.g., constructed of a material providing the appropriate flexibility, yet also providing stability upon insertion in the incision site) and may be adaptable for placement into incisions of various dimensions and locations (e.g., as illustrated in FIG. 1). In some aspects, sheath 42 has a generally tubular shape, e.g., an extruded tubular structure. Additionally, sheath 42 and/or retractors 48 may comprise a polymer or copolymer that has sufficient rigidity to support implantation of implant 12 while employing a thin-wall construction that can be collapsed, folded, broken or peeled-away without displacing implant 12. Exemplary materials suitable for such sheaths and retractors include, but are not limited to, nylon, polyethylene, polyurethanes, polyamides, fluoropolymers such as, e.g., polytetrafluoroethylene (PTFE), polyolefins, polyetheretherketones (PEEK), and flexible acrylics, and combinations thereof. The linear extrusion process of materials such as polytetrafluoroethylene may incorporate perforate line 44 (e.g., an intrinsic line of separation), e.g., due to the process or molecular orientation of the extruded material.

In some aspects of the present disclosure, retractor(s) 48 or sheath 42 may comprise a reinforced ring (not shown) that allows unrestricted movement of surgical tools used to create the tissue pocket (e.g., breast pocket) and to introduce implant 12. The reinforced ring may be flexible or rigid, and may include a slick or lubricious surface to reduce friction, e.g., to facilitate the introduction of implant 12 with a lower risk of abrasion or friction against implant 12. In combination with implants having biocompatible surface characteristics as discussed above (including, e.g., Motiva Implant Matrix® SilkSurface™ and VelvetSurface™ implants), retractor(s) 48 may allow implant 12 to be introduced into the tissue pocket while minimizing trauma to the surrounding tissue. Retractors 48 according to the present disclosure may be used for any location of the incision, such as incisions for inframammary, peri-areolar or trans-axillary implantation procedures (see, e.g., FIG. 1).

FIGS. 7A and 7B illustrate another exemplary introducer device 50 according to aspects of the present disclosure, in which chamber 18 (or chamber 22) is not secured to introducer device 50. In such a device, chamber 18 or 22 may be omitted completely, or alternatively, may be used to compress, elongate, or otherwise transition or maintain implant 12 in the insertion configuration (see, e.g., FIG. 2). Once implant 12 has been positioned in the insertion (e.g., reduced profile) configuration, chamber 18 or chamber 22 may be used to insert implant 12 into a shaft 52 of introducer device 50 (e.g., prior to connection of nozzle 110 via ring 106). Once received within shaft 52, chamber 18 or 22 may be discarded or sterilized and reused. Shaft 52 may include any of the features or dimensions of shaft 16 above.

Introducer device 50 may have a similar construction and manner of use as introducer device 10. As such, introducer device 50 includes a shaft 52 extending from a handle 54 (e.g., a squeeze-type or compression handle) including a first arm 56 rotatable about a pivot 58 (e.g., a dowel rod) (see FIG. 7B) and movable toward a second arm 60. First arm 56 is biased away from second arm 60 via a bracket 62 and torsion spring 64 supported by a dowel rod 65, as shown in FIG. 7B. To compress handle 50, a medical professional may first overcome the force imparted by spring 64. Handle 54 includes first (e.g., left) half portion 54A and second (e.g., right) half portion 54B positioned on opposite sides of a plane extending along longitudinal axis L. Housed within first half portion 54A and second half portion 54B are a pair of lock plates 66 on opposite sides of a plunger rod 68. Each lock plate 66 secures a shaft base 70 to a respective one of first half portion 54A and second half portion 54B via a plurality of fasteners (e.g., screws 72). First half portion 54A and second half portion 54B are each coupled to a respective cover 82 and 84, as shown in FIG. 7A and FIG. 7B.

Plunger rod 68 includes a proximal end coupled to (e.g., threadably, adhesively, etc.) a T-handle 86 which may be sized to enable grasping by a medical professional as needed and/or desired. A distal end of plunger rod 68 is coupled to a plunger head 88. Plunger head 88 includes a pair of circumferentially extending channels or grooves 90 and 92, within each of which a respective one of a pair of o-rings 94 and 96 is received. O-rings 94 and 96 prevent fluid (e.g., lubrication, aspiration, and/or irrigation fluid from passing proximally of plunger head 88. Additionally, proximal end of shaft 52 includes a portion 98 releasably coupleable to a proximal lock or ring 100, e.g., via threads or other complementary mating features of an internal surface of ring 100. For example, portion 98 may include threads and the internal surface of ring 100 may be correspondingly threaded. That is, each of threaded portion 98 and ring 100 may include a thread profile having a matching pitch and/or orientation. Upon connection of portion 98 and ring 100, a gasket 102 is compressed between and/or about a periphery of shaft base 70 so as to secure shaft base 70, and thereby handle 54, to shaft 52. A distal end of shaft 52 includes a portion 104 releasably coupleable to a distal lock or ring 106, e.g., via complementary mating features. For example, portion 104 may include threads and the internal surface of ring 106 may be correspondingly threaded. That is, each of portion 104 and ring 106 may include a thread profile having a matching pitch and/or orientation. Upon connection of portion 104 and ring 106, a gasket 108 is compressed between and/or about a periphery of a proximal end of a nozzle 110 so as to secure nozzle 110 to shaft 52.

Nozzle 110 may be formed from or otherwise include a pliable polymer (e.g., polyurethane, polyethylene, silicone, etc.), which may be rigid enough to dilate an incision site, but soft enough to avoid tearing or damaging the site. An opening 112 at the distal end of nozzle 110 may have any suitable shape, such as, e.g., round, oval, half-oval (e.g., having one side that is flat and another side that is rounded or oval), or angular in shape. The shape of nozzle 110 may be selected to accommodate the shape of implant 12 to be introduced into a patient (e.g., a half-oval or angular shape to accommodate a non-round implant). Nozzle 110, as shown in FIGS. 7A and 7B, is tapered such that a distal end diameter is smaller than a proximal end diameter of nozzle 110. Additionally, the length of nozzle 110 may be varied, as needed or desired. For example, the degree or angle of taper, diameter of the distal opening, and length of nozzle 110 may be selected so as to correlate to, and to accommodate, differently sized implants. In use, a medical professionally may deliver implant 12 (not shown in FIGS. 7A and 7B) loaded within shaft 52 via actuation of handle 54 to advance plunger head 88 towards nozzle 110. As plunger head 88 is advanced distally, implant 12 is pushed through opening 112 and delivered into the breast pocket of a patient.

Figure 8B:
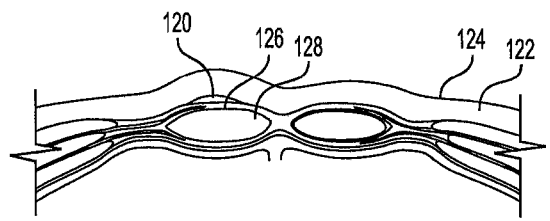

As noted above, implant 12 may be inserted through an umbilicus incision 8 to minimize visible scarring. In such a procedure, incision 8 is typically made in the umbilicus to introduce a blunt dissecting instrument to form a tunnel 120 (see FIGS. 8A and 8B), over which a larger cannula or tube is inserted and advanced to a tissue pocket 130 where implant 12 is to be positioned. Forming tunnel 120 separates subcutaneous tissue 122 (e.g., fat located under the skin 124) from the rectus sheath 126 positioned anterior of the rectus abdominis muscle 128.

A challenge associated with this approach is compressing implant 12 sufficiently to be "pushed" through tunnel 120. Typically, the cannula used to form tunnel 120 is too small in diameter to deliver current implant 12 designs, such that the cannula only serves to establish a subcutaneous tunnel. After formation of tunnel 120, implant 12 is advanced through tunnel 120, which imparts many additional forces and stresses on implant 12, thus increasing the probability of damage to implant 12, such as rupture of shell 14.

To improve patient safety and reduce the trauma to implant 12 and subcutaneous tissues 122 of the patient associated with such procedures, an introducer system employing one or more of the features of the examples above may be used. For example, introducer device 10 or introducer device 50 may be used in conjunction with a tunneling sheath 132 (see FIGS. 9A-9B and 10A-10C). Alternatively, any introducer device herein described may be used instead of introducer device 10. Introducer device 10 (or any other described introducer device) as well as tunneling sheath 132 includes a length sufficient to reach the intended area (e.g., breast pocket 130) for implantation from umbilicus incision 8 (see, e.g., FIG. 1).

Figure 9A:
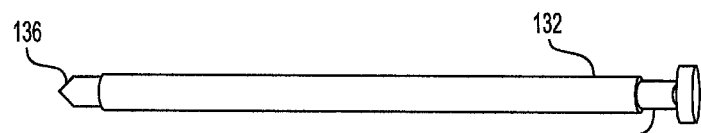
FIGS. 9A and 9B illustrate a system for forming a tunnel and delivering an implant during a procedure, according to aspects of the present disclosure.
Figure 9B:
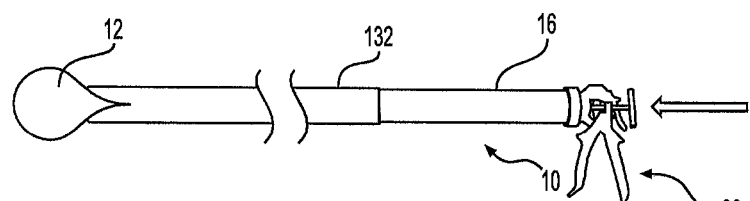

For example, as shown in FIGS. 9A and 9B, tunneling sheath 132, having a dimension or length sufficient to extend from incision 8 to breast pocket 130, and having an internal diameter sufficient to receive therein shaft 16 of insertion device 10 and/or implant 12 in the insertion configuration (e.g., reduced profile configuration) is advanced through incision 8 to breast pocket 130. The diameter of tunneling sheath 132 may correlate to the size of an incision, and as such, may be between about 1.0 cm and about 3.0 cm, e.g., between about 1.5 cm and about 2.5 cm, e.g., about 1, 1.5, 2, 2.5, or 3 cm. To enhance the stability and pushability of tunneling sheath 132, an inner trocar 134 or cannula (having a smaller diameter) may be used (FIG. 9A). That is, inner trocar 134 may be inserted through a lumen of tunneling sheath 132 and both may be simultaneously advanced through tunnel 120. A blunt distal end 136 of inner trocar 134 may separate tissues to form tunnel 120. Inner trocar 134 and tunneling sheath 132 form a coaxial system to facilitate insertion and advancement of implant 12. Once the tunneling sheath 132 is properly positioned, inner trocar 134 may be removed to allow for access to a lumen extending through tunneling sheath 132. Next, shaft 16 of insertion device 10 may be inserted into the channel of tunneling sheath 132 (FIG. 9B) so as to advance implant 12 through tunneling sheath 132, and may be actuated as discussed above, to advance implant 12 into breast pocket 130. Such an insertion approach may minimize the entry wound/incision and length of travel from the entry incision to breast pocket 130. Smaller incisions and tunnel 120 lengths may reduce trauma and result in faster healing rates and fewer complications.

Figure 10A:
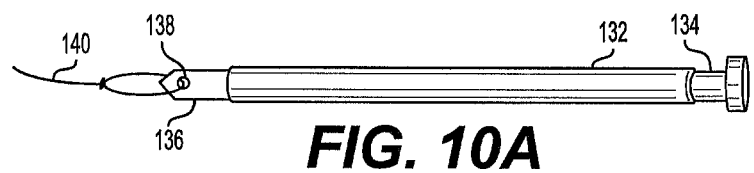
FIGS. 10A-10C illustrate another exemplary system for forming a tunnel and delivering an implant during a procedure, according to aspects of the present disclosure.
Figure 10B:
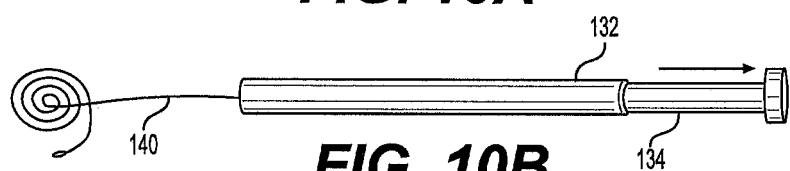
Figure 10C:
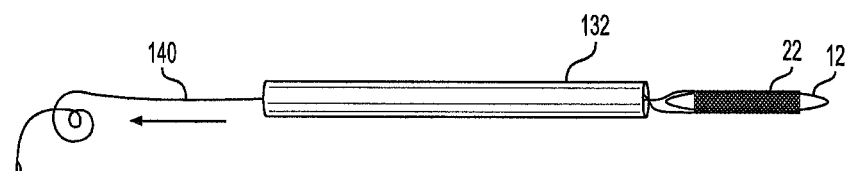

In some aspects, blunt distal end 136 of trocar 134 may include features for attachment of a suture or thread. For example, distal end 136 may include an eyelet 138, as shown in FIG. 10A. A line 140 such as a monofilament thread having a small diameter is secured to eyelet 138 and pulled through tunneling sheath 132 with trocar 134 (FIG. 10A). A small incision or opening through or proximate to breast pocket 130 enables a medical professional to grasp and thread line 140 from the breast pocket 130, through the opening, and exterior of the patient's body for handling, e.g., pulling, by the medical professional. Exemplary materials for line 140 include, but are not limited to, polymers, fibers (e.g., similar to suture material or a fishing line), and metals or metal alloys, such as metallic wire. Following formation of tunnel 120 and threading at least a portion of line 140 through the opening in the breast pocket 130, trocar 134 may be withdrawn through the lumen of tunneling sheath 132, thereby pulling a portion of line 140 therewith. As such, at least a portion of line 140 is left in tunnel 120 (FIG. 10B) established by the trocar 134 once trocar 134 is removed. Line 140 then may detached, e.g., untied, from eyelet 138 and later secured to a separate bag, sack, or chamber 22 (or optionally chamber 18) in which implant 12 is housed in the insertion configuration. Once coupled, the medical professional may gently pull implant 12 (within the separate bag, sack, or chamber, e.g., chamber 22 or 18) through tunnel 120 from the opposing end (FIG. 10C). Additionally or alternatively, upon removal of trocar 134, an elongated plunger (not shown) may be used to advance (e.g., push) implant 12 through the lumen of tunneling sheath 132 until implant 12 exits the distal end of tunneling sheath 132 and expands towards the deployed configuration within the breast pocket 130.

As mentioned above, introducer devices described herein (e.g., introducer devices 10, 50) may be used for implantation of implant 12 with visco-elastic and/or highly elastic properties, e.g., comprising an elastic shell and visco-elastic silicone gel. Such elastic properties of implant 12 enable implant 12 to be stretched or elongated for loading into a chamber (e.g., chamber 18, chamber 22, etc.) in a reduced profile for implantation in a minimally-invasive manner with less trauma to the patient. For example, various properties of implant 12 may allow for uniform radial compression of implant 12, which may provide an ability to safely compress implant 12 for advancement into a smaller incision (e.g., an incision of less than about 3.0 cm) than is conventionally used in the implantation procedure.

As noted above, a plunger (e.g., plunger rod 38 or 68 having a plunger head 88, etc.) may be used for pushing or urging the compressed implant 12 from the introducer device through a tapered funnel or nozzle (e.g., nozzle 110, FIGS. 7A-7B) and into the incision site. In some examples, and depending on the type and features of the implant, for example, this pushing mechanism may impose a significant load on a proximal portion of implant 12, e.g., creating excessive pressure between implant 12 and the introducer device (e.g., an inner wall of shaft 16 or shaft 52). In some cases, the pressure may lead to a rupture of shell 14 of implant 12, and/or may cut, sever, or otherwise deform implant 12 upon expulsion from the introducer device (e.g., introducer device 10, introducer device 50, etc.).

In some arrangements, a fluid barrier between the plunger head (e.g., plunger head of plunger rod 38, plunger head 88 of plunger rod 68, etc.) and implant 12 may be used to at least partially alleviate pressure between implant 12 and the introducer device. Depending on the type of implant and/or introducer device, however, mechanical pressure may cause water or other fluid (e.g., saline solution) to flow around circumferential edges and/or creases or fold of implant 12 and/or leak out of a distal portion of the selected introducer device. Such leaking water or fluid, however, may impart additional pressure to implant 12, such that implant 12 may be further compressed thus further elongating implant 12 and/or reducing a diameter of implant 12.

In some aspects of the present disclosure, an introducer device may use compressed gas (e.g., $CO_2$, air, or other suitable inert gas) to advance implant 12 from inside a shaft and/or a chamber, and through a tapered nozzle located at a distal end of the introducer device. For example, the gas may provide a buffer between implant 12 and the walls of the introducer device shaft similar to water. In a manner similar to the leaking water flow example discussed above, compressed gas may leak around the circumference of implant 12 as it is urged out of the distal end of the device. However, the pressure from the compressed gas may help further radially-compress the implant as the continuous air pressure pushes implant 12 from the proximal end of the introducer device toward the nozzle at the distal end of the device chamber.

Figure 11:
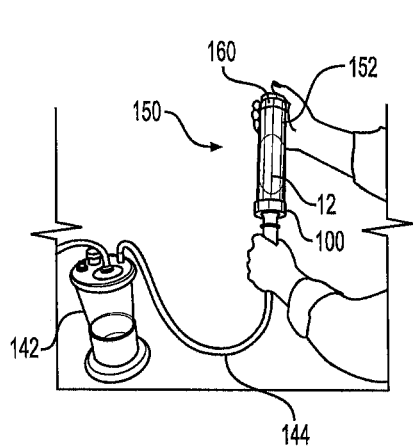
FIGS. 11 and 12 illustrate an exemplary introducer device coupled with a compressed gas source, according to aspects of the present disclosure.
Figure 12:
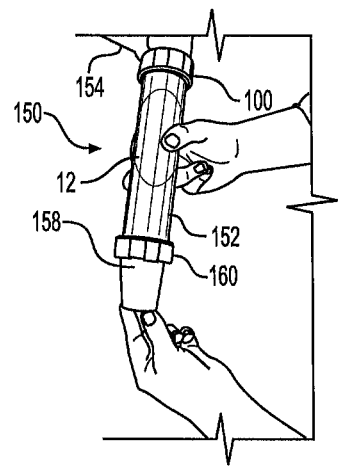

In some aspects of the present disclosure, a compressed gas source 142 may be used to pull an implant into a shaft (similar to shaft 16, shaft 52, etc.) of the introducer device. The implant may be lubricated, e.g., comprising a lubricant on the surface of the implant. For example, as shown in FIG. 11, ring 100 of introducer device 150 may be unscrewed or otherwise uncoupled from handle 154 and fluidly coupled to compressed gas source 142 (e.g., a negative pressure source referred to as a venturi vacuum) via any appropriate conduit 144. Additionally, nozzle 158 may be uncoupled from shaft 152 by unscrewing or otherwise uncoupling ring 160 from shaft 152. Shaft 152 may include any of the features or dimensions of shaft 16 and/or 52 above. Once so arranged, a distal end of shaft 152 (e.g., an end closer to ring 160) may be positioned near, adjacent to, or in contact with implant 12 (e.g., having a lubricated shell 14 as discussed above). Next, compressed gas source 142 may be activated in any appropriate manner so as to pull, suck, or otherwise draw implant 12 into shaft 152 through the distal end of shaft 152. Once received within shaft 152, ring 100 may be unscrewed or otherwise uncoupled from conduit 144 and compressed gas source 142, and then may be coupled to handle 154, as discussed above. Additionally, nozzle 158 may be coupled to the distal end of shaft 152 via ring 160. While FIGS. 11 and 12 refer to components of introducer device 150, the disclosure is not so limited. Rather, a proximal end of the shaft 16 of introducer device 10 may likewise be coupled to compressed gas source 142 to draw implant 12 through a distal end of shaft 16 (e.g., following removal of compression ring 26 and chamber 18 or chamber 22).

Alternatively, following drawing implant 12 into shaft 152, compressed gas source 142 may remain coupled to shaft 152 and switched or toggled in a reverse direction so as to produce a positive pressure source to force or push implant 12 so as to expel implant 12 from shaft 152 and into an appropriate implantation location (e.g., breast pocket 130) of a patient. In order to facilitate switching between negative and positive pressure types (e.g., a direction of flow of compressed gas), compressed gas source 142 and/or introducer device 150 may utilize a valve mechanism (not shown) that allows the user to switch between these two functions. In other words, compressed gas source 142 may be used to both load and expel implant 12 from introducer device 150. Thus, the device may provide a self-contained system equipped to provide a vacuum or expulsion pressure, as opposed to connecting different wall attachments for vacuum or compressed air/gas. In at least one example in which compressed gas source 142 is used to expel implant 12, handle 154 need not be reattached to shaft 152 via ring 100.

FIG. 13 illustrates various features of exemplary introducer device 150 according to aspects of the present disclosure. Introducer device 150 may be a self-contained introducer device including a shaft 152 having a handle 154 coupled to a first (e.g., proximal end) of shaft via a ring 156 and a tapered nozzle 158 coupled to a distal end of shaft 152 via a ring 160. As shown in FIG. 13, a disposable compressed gas cartridge 162 (e.g., a compressed $CO_2$ or air cartridge) is coupled to handle 154 via any suitable connector or adaptor, and may be replaced as needed to replenish the source of compressed gas. Handle 154 includes a toggle or switch 164 actuatable to alternate between vacuum and expulsion pressure generated with the compressed gas cartridge 162. The mechanism may include a toggle switch for changing between a vacuum mode and a pressure mode. Additionally, handle 154 includes a trigger 166 or other suitable actuator for generating the vacuum or pressure.

Nozzle 158 may be disposable and may comprise a biocompatible material, such as a pliable polymer (e.g., a polyurethane, polyethylene, silicone, etc.) that is rigid enough to dilate an incision site, but soft enough to avoid tearing or damaging the incision site. Similar to nozzle 110, a distal opening 168 of nozzle 158 may have any suitable shape, such as, e.g., round, oval, slitted-duckbill, half-oval (e.g., having one side that is flat and another side that is rounded or oval), or angular in shape to accommodate implant 12 to be implanted. The dimensions of nozzle 158 (e.g., length and distal diameter) may be selected in accordance with the dimensions and/or requirements of implant 12.

Switch 164 may include a mechanism by which the medical professional may select a negative pressure (e.g., the venturi vacuum) to pull implant 12 into shaft 152 of introducer device 150 (e.g., prior to attachment of nozzle 158), and then actuate switch 164 to reverse the valve mechanism to provide compressed gas for expelling implant 12. Other such vacuum effects can be generated by known displacement or rotary vacuum mechanisms. It is also contemplated that trigger 166 and/or switch 164 may be electrical or digital, and operate by sending signals to one another and/or to the valve mechanism to move between the negative (e.g., vacuum) and positive pressure configurations, and to actuate the dispensing of compressed gas from cartridge 162.

FIGS. 14 and 15 are a schematic views of a proximal portion of an introducer device during the vacuum configuration or mode that may be used to load an implant into the delivery chamber of the introducer device. As shown, when switch 164 (FIG. 13) is set to the vacuum configuration, a user may pull trigger 166 (FIG. 13) to cause compressed gas to move from cartridge 162, through an opening 170 in a circumferential side surface of the device. Optionally, opening 170 may include an inlet conduit as shown in FIG. 15. Once the gas moves through opening 170, the valve mechanism urges gas proximally through and out of the device via an exhaust port 172 positioned at the proximal end of the device. Operating the device in this manner may have the effect of a vacuum on portions of the introducer device 150 that are distal to opening 170 (e.g., shaft 152 within which implant 12 may be loaded). By toggling switch 164 to the pressure/dispensing configuration or mode, the valve mechanism may be altered such that once the compressed gas moves from cartridge 162 and through opening 170, the gas may be directed distally through shaft 152 to urge implant 12 distally out of introducer device 150. In some aspects, introducer device 150 may further include a pressure relief valve to relieve excess pressure within shaft 152.

Figure 16A:
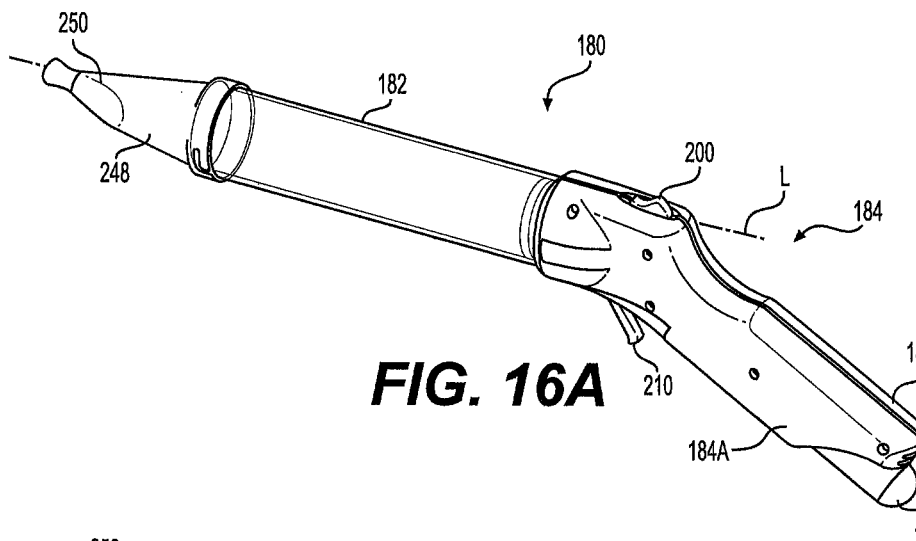
FIGS. 16A and 16B illustrate another introducer device, according to aspects of the present disclosure.
Figure 16B:
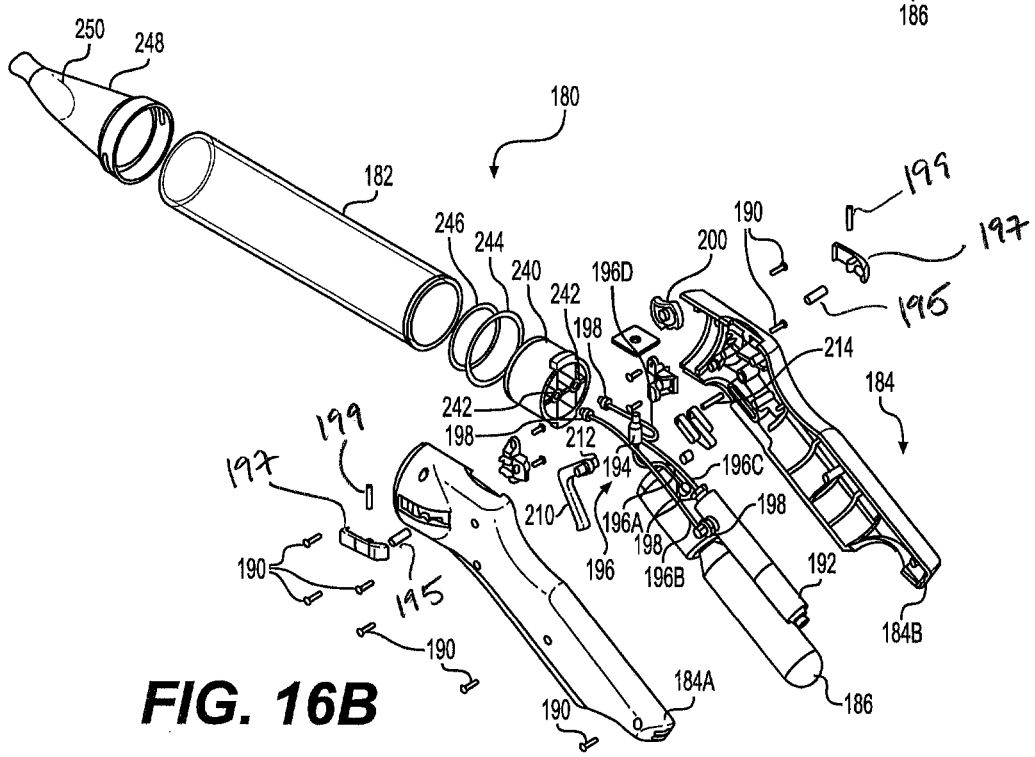

FIGS. 16A and 16B illustrate a further exemplary introducer device 180 according to aspects of the present disclosure. Introducer device 180 may have a similar construction and manner of use as introducer device 150 (e.g., FIG. 13). For example, similar to introducer device 150, introducer device 180 includes a compressed gas cartridge 186. Handle 184 includes first (e.g., left) half portion 184A and second (e.g., right) half portion 184B positioned on opposite sides of a plane extending along longitudinal axis L and coupled together via a plurality of connectors (e.g., screws 190). In addition to compressed gas cartridge 186, housed within first half portion 184A and second half portion 184B is a pump 192. Pump 192 may include any appropriate pumping mechanism such a reciprocal or rotary pump. As shown in FIG. 16B, each of compressed gas cartridge 186 and pump 192 is fluidly coupled to a valve mechanism 194 via one or more conduits 196 (e.g., conduits 196A-196D).

For example, conduits 196A and 196D may control pressure, and conduits 196B and 196C may control suction, e.g., through a venture vacuum. Additionally, each end of each conduit 196A-196D may include a fitting 198 to fluidly couple and secure a respective one end of each conduit 196A-196D to one or more of compressed gas cartridge 186, pump 192, valve mechanism 194, and shaft 182, as shown in FIG. 16B. Shaft 182 may include any of the features or dimensions of shaft 16, 52, and/or 152 above.

Handle 184 includes a toggle or switch 200 (also referred to herein as a mode selector) actuatable to alternate between vacuum and expulsion pressure (e.g., a vacuum mode and pressure mode) generated with the compressed gas cartridge 186. The switch 200 may include a toggle switch for adjusting valve mechanism 194 between a vacuum mode and a pressure mode. A lower surface of switch 200 may define a cam surface that contacts valve 194 to switch between a suction mode and a pressure mode, e.g., via conduits 196B and 196C, and conduits 196A and 196D. As such, in a first orientation of switch 200 relative to handle 184, valve mechanism 194 is arranged to generate vacuum pressure in shaft 182. In a second orientation of switch 200 relative to handle 184, valve mechanism 194 is arranged to positive expulsion pressure in shaft 182.

Additionally, handle 184 includes a trigger 210 for generating vacuum or positive pressure in shaft 182. As shown, for example, trigger 210 may include an L-shaped bracket or arm having one end 212 pivotably coupled to handle 184 via shaft or dowel rod/pin 214. Additionally, trigger 210 is coupled to valve mechanism 194. Further, as shown in FIG. 16B, handle 184 includes locking levers 197 that secure the proximal end of shaft 182 to handle 184. Each locking lever 197 pivots about a pin 199 extending through an aperture of locking lever 197 and is coupled to a spring 195. By pivoting locking levers 197 radially outward about pins 199, the ends of locking levers 197 may release from a circumferential groove at the proximal end of shaft 182 to release shaft from handle 184. Thus, handle 184 may be detached from shaft 182 following a procedure and be reused, following sterilization of handle 184, e.g., via autoclave.

Further, handle 184 includes a core seal 240 retained between first half portion 184A and second half portion 184B. Core seal 240 may comprise any appropriate material such as, for example, a polymer, rubber, or the like. As shown in FIG. 16B, one or more of fittings 198 may be coupled to a lumen 242 extending through core seal 240 so as to deliver negative and/or positive pressure to shaft 182. A distal portion of core seal 240 is at least partially received within a lumen of shaft 182 while a remainder of core seal 240 is received within handle 184. An o-ring 244 is positioned about a circumference of core seal 240, such that, upon coupling of core seal 240 and handle 184, o-ring 244 is received within an internal channel of handle 184 and prevents fluid (e.g., gas) from leaking proximally of o-ring 244. A second o-ring 246 is positioned about a circumference of core seal 240 and distally of o-ring 244. Upon coupling of core seal 240 and shaft 182, o-ring 246 is received within the lumen of shaft 182 and prevents fluid (e.g., gas) from leaking proximally of o-ring 246. Beyond prevention of proximal egress of gas or fluid, o-rings 244 and 246 may facilitate securing shaft 182 to handle 184. Additionally, a distal end of shaft 182 is releasably coupleable (e.g., via an interference fit, threaded coupling, etc.) to a proximal a proximal end of a nozzle 248 so as to secure nozzle 248 to shaft 282.

Similar to nozzle 110, described above, nozzle 248 may be formed from or otherwise include a pliable polymer (e.g., polyurethane, polyethylene, silicone, etc.), which may be rigid enough to dilate an incision site, but soft enough to avoid tearing or damaging the site. An opening 250 at the distal end of nozzle 248 may have any suitable shape, such as, e.g., round, oval, half-oval (e.g., having one side that is flat and another side that is rounded or oval), or angular in shape. The shape of nozzle 248 may be selected to accommodate the shape of implant 12 to be introduced into a patient (e.g., a half-oval or angular shape to accommodate a non-round implant). Nozzle 248, as shown in FIGS. 16A and 16B, is tapered such that a distal end diameter is smaller than a proximal end diameter of nozzle 248. Additionally, the length of nozzle 248 may be varied, as needed or desired. For example, the degree or angle of taper, diameter of the distal opening 250, and length of nozzle 248 may be selected so as to correlate to, and to accommodate, differently sized implants 12. For example, a tapered nozzle (e.g., nozzle 110, 158, 248, or 298 (described below)) may facilitate implantation of implant 12 in a desired orientation or "right side up" manner. The diameter of such a nozzle may vary to accommodate varying sized implants and correlate with a size or location of an incision through which the implant is to be delivered. In at least one example, the nozzle may have an angled aperture, e.g., providing a larger opening for implant to exit.

In use, a medical professional may remove (if not already done) nozzle 248 from the distal end of shaft 182 and toggle switch 200 to the vacuum mode. Then, the distal end of shaft 182 may be positioned near, adjacent to, or in contact with implant 12 (e.g., having a lubricated shell 14 as discussed above). Next, compressed gas source 186 may be activated via trigger 210 as to pull, suck, or otherwise draw implant 12 into shaft 182 through the distal end of shaft 182. Once implant 12 is housed within shaft 182, switch 200 may be toggled to the pressure mode (e.g., expulsion mode) and nozzle 248 may be coupled to the distal end of shaft 182, as noted above. Next, nozzle 248 may be positioned within, through, or near the incision site and compressed gas source 186 may be activated via trigger 210 as to push, force, or otherwise expel implant 12 from shaft 182, through nozzle 248, and into the patient (e.g., into breast pocket 130).

Compressed gas sources 162, 186 may have any appropriate volume and dimensions so as to contain and connect compressed gas to a respective introducer device (e.g., introducer device 150, introducer device 180). For example, either or both of sources 162 and 186 may include a total length of about 88.4 mm (approximately 3.5 inches), and a total width (e.g., diameter) of about 22 mm (approximately 0.875 inches). A neck or connection between source 162, 186 and a remainder of introducer device 150, 180, respectively may have a length of about 9 mm (approximately 0.375 inches) and a width (e.g., diameter) of approximately 9 mm (approximately 0.375 inches). These dimensions are exemplary only and may vary depending on other dimensions of the introducer device and/or volume of compressed gas desired or required. Additionally, in some aspects, introducer device 180 may further include a pressure relief valve to relief excess pressure within shaft 182.

Figure 17A:
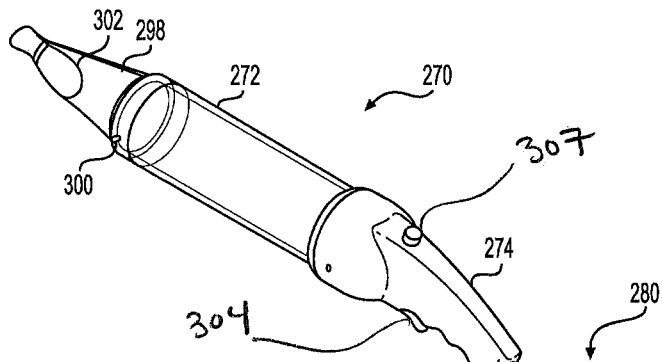
FIGS. 17A and 17B illustrate a further introducer device, according to aspects of the present disclosure.
Figure 17B:
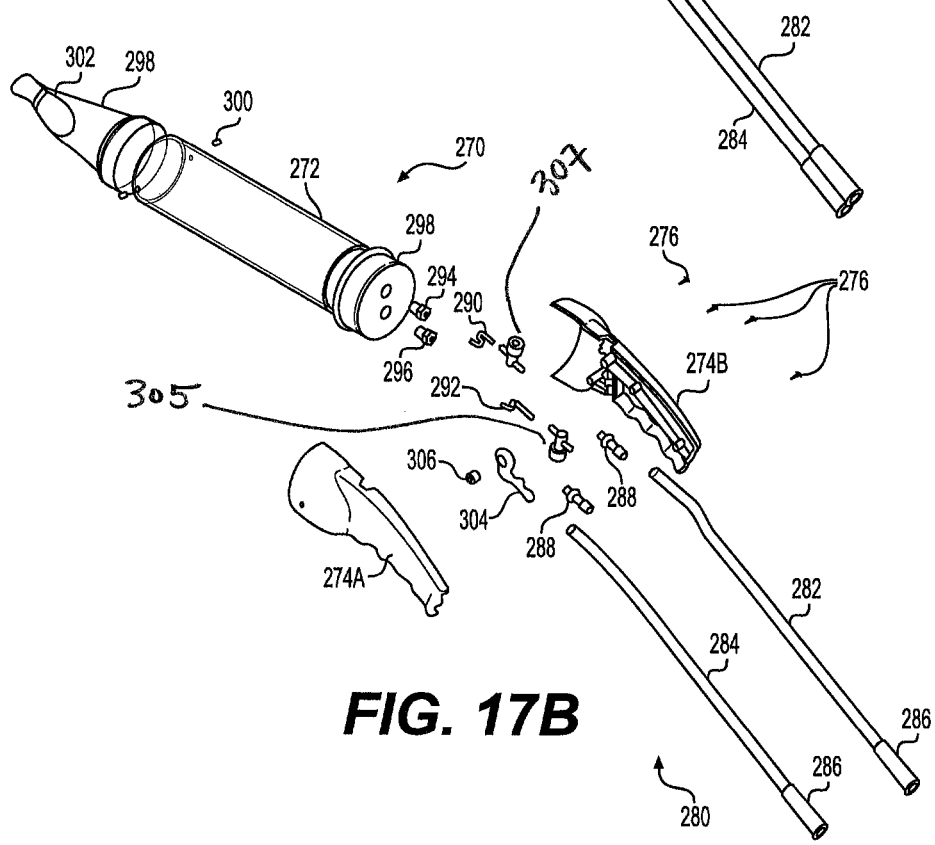

FIGS. 17A and 17B illustrate a further exemplary introducer device 270 according to aspects of the present disclosure. Introducer device 270 may have a similar construction and manner of use as introducer device 180 (e.g., FIGS. 16 and 16B), except compressed gas source 186 and pump 192 have been replaced with tubing assembly 280, coupleable to a source of compressed gas, such as facility gas supplies (e.g., hospital or medical center building-supplied gas sources via utility hookups). In some examples, introducer device 270 may be single-use or disposable.

For example, tubing assembly 280 includes a suction line 282 and a positive pressure line 284. Each of suction line 282 and pressure line 284 includes a fitting 286 on a proximal end thereof for connection to the facility gas supplies (not shown) and a fitting 288 (e.g., luer adapter) for connection to a corresponding connection line of the introducer device 270. For example, fitting 288 of suction line 282 is coupled to a first end of suction connection 290 while fitting 288 of pressure line 284 is coupled to a first end of pressure connection 292. Additionally, a second end of suction connection 290 is coupled to a fitting 294 of a core seal 298 while a second end of pressure connection 292 is coupled to a fitting 296 of core seal 298. As shown, core seal 298, in turn, is received within handle 274, e.g., between shaft 272 and handle 274. Shaft 274 may include any of the features or dimensions of shaft 16, 52, 152, and/or 182 above. As shown, handle 274 includes first (e.g., left) half portion 274A and second (e.g., right) half portion 274B coupled together via any appropriate manner such as, e.g., via screws 276. Additionally, a distal end of shaft 272 is releasably coupleable (e.g., via an interference fit, threaded coupling, pins 300, etc.) to a proximal end of a nozzle 298 so as to secure nozzle 298 to shaft 272. Nozzle 298 may be similar in shape and construction as nozzle 248, described above.

Further, handle 274 includes two actuators to control suction and vacuum. For example, handle 274 may include a first actuator, trigger 304 (e.g., controlled by an index finger of the user) for generating one of vacuum or positive pressure in shaft 272, and a second actuator, e.g., actuator 307 (e.g., controlled by a thumb of the user) for generating the other of vacuum or positive pressure. Actuator 307 may extend through the handle and define a portion of a valve. As shown, trigger 304 is rotatably coupled to handle 274 via bearing 306, which controls valve 305, e.g., trumpet valve 305. In at least one example, In some aspects, introducer device 270 may further include a pressure relief valve to relief excess pressure within shaft 272.

In at least one example, the trigger 304 controls pressure and the second actuator 307 controls suction. In some examples, both actuators may be pressed simultaneously to apply both pressure and suction. For example, actuator 307 may fluidly couple suction line 282 with shaft 272, and trigger 304 may fluidly coupled pressure line 284 with shaft 272. In such an arrangement, each of the suction and pressure may be applied to shaft 272 simultaneously, if so desired. For example, to reduce the degree of suction applied via actuation of actuator 307, a medical professional may press trigger 304 to fluidly couple pressure line 284 with shaft 272.

In use, a medical professional may remove (if not already done) nozzle 298 from the distal end of shaft 272 and fluidly couple suction line 282 with shaft 272. Then, the distal end of shaft 272 may be positioned near, adjacent to, or in contact with implant 12 (e.g., having a lubricated shell 14 as discussed above). Next, trigger 210 may be actuated so as to pull, suck, or otherwise draw implant 12 into shaft 272 through the distal end of shaft 272. Once implant 12 is housed within shaft 272, pressure line 284 may be fluidly coupled with shaft 272. Next, nozzle 298 may be coupled to the distal end of shaft 272, as noted above, and nozzle 298 may be positioned within, through, or near the incision site. Trigger 210 then may be actuated so as to push, force, or otherwise expel implant 12 from shaft 272, through nozzle 298, and into the patient (e.g., into breast pocket 130).

In some arrangements, the introducer devices described herein (e.g., introducer devices 150, 180, 270, etc.) may adapt to a sterile packaging system to provide a "touchless" implantation procedure. That is, the physician, nurse, or other medical professional or user need not directly handle implant 12 when loading the implant 12 into the introducer device (e.g., introducer devices 150, 180, 270, etc.) or at other times during implantation.

For example, as shown in FIGS. 18 and 19, a separate sterile package 320 may be sized and/or shaped so as to contain implant 12 therein. As illustrated, package 320 may have the shape of a hemisphere with a diameter suitable for enclosing a specified sized and volume of implant 12 (e.g., a breast implant). In some examples, a pull-tab opening 322 may be integrated into either side of the sterile package 320. The opposing side may be covered by a Tyvek material used in packaging sterile medical devices or other suitable material for sterile packaging. The Tyvek lid or other portion of the package may also include a separate injection port (not shown) that may further accommodate injection of sterile saline and/or lubricant.

As shown in FIG. 20, for example, package 320 may be used in conjunction with introducer device 150. Alternatively, package 320 may be used in conjunction with any introducer device described herein. In some examples, package 320 may include features complementary to features of a nozzle (e.g., nozzle 110, nozzle 158, nozzle 248, nozzle 298, etc.) or a distal end of a shaft (e.g., shaft 16, shaft 52, shaft 152, shaft 182, shaft 272, etc.) to allow the introducer device to connect to package 320. For example, the distal end of the shaft 152 of introducer device may be threaded (or have other mating features) to allow the connection of the distal end of shaft 152 to package 320 via complementary threads (or other complementary mating features) of package 320. In some examples, the introducer device may include counter-threads or connection tabs located within the shaft 152. For example, threads may be thermoformed into the outer surface of package 320 that contains implant 12.

In other examples, package may include a reduced diameter opening to receive shaft 152. Optionally, package 320 may include an o-ring (as illustrated in FIG. 20) to provide for a better seal between shaft 152 and package 320.

Package 320 may be designed in such a way that the user can use a pull-tab 322 to open the sterile package (similar to opening a sealed can), providing access to the enclosed implant 12. Pull-tab may be located on the curved portion of package 320, as shown in FIGS. 18-20, or may be located on the opposite, substantially planar, portion of package 320. For example, in some examples, pull tab may be removed from the planar portion of package 320 and the implant drawn into shaft 152.

While package 320 is opened, and prior to the connection of package 320 to the shaft 152, the user can inject sterile saline and/or lubricant into package 320 to aid in the movement of implant 12 into shaft 152. Once the connection between package 320 and shaft 152 is secured, the vacuum mode of the system may be used to then pull the lubricated, sterile implant 12 into shaft 152, to prepare implant 12 for injection into the incision site. Mating features or mechanisms other than threads may be used to connect the shaft 152 to sterile package 320. This loading system may help avoid any physical contact or minimize physical contact of implant 12 with the user and/or the surrounding environment, thereby reducing or eliminating the risks of puncture or introduction of particulate debris to the surface of implant 12.

Following experimentation, appropriate expulsion pressures to expel implant 12 from an introducer device may correlate to i) the volume/size of implant 12, ii) the incision location and size, and iii) the nozzle diameter of the introducer device that is inserted within the incision. A chart may be provided to the end-user that defines these correlations for optimal device placement. The chart may be developed by bench and pre-clinical assessments, for example.

By way of example only, assuming implant 12 makes a perfect seal against an inner surface of the shaft (e.g., shaft 16, 52, 152, 182, 272, etc.), the volume of gas/fluid sufficient to expel implant 12 may be equal to the implant volume (up to 925 cc (cubic centimeters)). An alternative way to calculate required air pressure to expel implant 12 is to determine the pressure needed to expel the entire volume of the shaft (e.g., shaft 16, 52, 152, 182, 272, etc.) (in one example, the dimensions of the shaft are approximately 2 inches (diameter) by 12 inches (length)), or about 625 cc. The same pressure may be used to vacuum load the implant into the chamber of the introducer device.

For some exemplary implantation procedures, 1000 cc or about 60 ci (cubic inches) is sufficient to propel an implant having a volume of up to about 925 cc. Thus, if the vacuum pump is 100% efficient, 60 ci of $CO_2$ (or other suitable gas) may be used to load implant into the shaft of the introducer device, and to subsequently propel implant from the shaft. Using Boyle's Law ($P_1V_1=P_2V_2$), along with the following assumptions, the chart below provides for the range of potential volumes of various compressed gas sources (e.g., source 162, source 186) that would supply sufficient gas pressure for loading and expulsion of a silicone gel implant with a range of volumes that require 30 psi:

A constant temperature at 70° F.
Gas supply minimum fill pressure of 800 psi
25 psi for both loading and expulsion of implant 12
12 g (3 inch) gas supply 18 cc (1 ci)

TABLE 1

| size | Volume @ STP (14.7 psi) | Volume @ 30 psi * |
|---|---|---|
| 12 g | 6 L | 3 L (183 ci) |
| 16 g | 8 L | 4 L (244 ci) |
| 20 g | 10 L | 5 L (305 ci) |
| 33 g | 17 L | 8 L (494 ci) |
| 45 g | 23 L | 11 L (671 ci) |

In addition, it is known that one mole of an ideal gas occupies a volume of 22.4 liters at STP (Standard Temperature and Pressure, 0° C. (273.15° K) and one atmosphere pressure (14.7 psi)). Using the following parameters, a 16 g gas supply may provide sufficient volumes and pressures for an average size breast implant procedure.

The ideal gas law PV=nRT may be used to calculate the volume of gas at atmospheric pressure for a given amount of gas, wherein:

P is the pressure of the gas (atm)
V is the volume of the gas (L)
T is the absolute temperature of the gas 273.15° K
R has the value: 0.08206 L·atm/(mol·K).
n is the number of moles of the gas (mass/molecular weight)

Accordingly, and by way of example only, for a gas supply containing 16 g of $CO_2$:

1 mole of $CO_2$ is 44 grams (i.e., molecular weight=44 g/mol)
n=(16 g)/(44 g/mol)=0.36 moles $CO_2$
P=1 atm
PV=nRT
V=about 8 liters (0.28 cubic feet) of $CO_2$ at 1 atm
To calculate the volume of gas for other pressures @ constant temperature: $P_1V_1=P_2V_2$.

Therefore, this system may provide for the use of disposable gas (e.g., $CO_2$, air, or air/CO2 mixtures) sources (e.g., 162, 186) in the range of 12-33 g and volumes from 180 ci to 500 ci, providing an average pressure of 30 psi for both the vacuum and expulsion processes during an implantation procedure.

The introducer devices described herein may be used to standardize and/or facilitate procedures for implantation of a breast implant or other such implant device. In some examples, the introducer device may be configured for one-handed advancement of the implant. Additionally, any one or more of the shafts (e.g., 16, 52, 152, 182, 272), chambers (e.g., 18, 22), tunneling sheath 132 or other such device may be constructed of a low-friction material, such as polytetrafluoroethylene (Teflon®), and/or coated with a highly lubricious (e.g., hydrophilic) material to reduce the coefficient of friction between the introducer device and implant 12. In some aspects, a combination of features of the implant and the introducer system may help to optimize a minimally-invasive procedure, e.g., to improve patient well-being. For example, a breast implant characterized by surface texturing, high elongation, high shell strength, and super visco-elastic and consistent silicone filling gel may be implanted with an introducer device as described above in a minimally-invasive insertion method to minimize scarring of the incision site, reduce the risk of damaging the implant during placement, and/or to accelerate and optimize healing of the surgical wound.

While principles of the present disclosure are described herein with reference to illustrative aspects for particular applications, it should be understood that the disclosure is not limited thereto. For example, as noted above, any of the disclosed introducer devices (e.g., introducer device 150, 180, or 270) described above may further include a pressure relief valve to relief excess pressure within a respective shaft (e.g., shaft 152, 182, or 272). Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

We claim:

1. A medical device for delivering a breast implant to a subject, comprising:
   a shaft extending between a proximal end and a distal end, the shaft including a lumen therein, the distal end including a tapered nozzle, wherein the shaft is configured to compress the breast implant has an inner diameter ranging from about 2-3 inches;
   a handle detachably coupled to the proximal end of the shaft and including a valve mechanism and an actuator; and
   a tubing assembly extending from a distal end of the handle and configured to transfer a fluid between a compressed fluid source and the shaft, the tubing assembly including a pressure line extending through a body of the handle;
   wherein the actuator is configured to engage the valve mechanism to control fluid flow to the shaft through the pressure line so as to impart a positive pressure in the at least a portion of the lumen.

2. The medical device of claim 1, wherein the nozzle comprises a polymer and is tapered towards a distal opening.

3. The medical device of claim 2, wherein the distal opening of the nozzle is ovular.

4. The medical device of claim 1, wherein the nozzle is removably coupled to the distal end of the shaft.

5. The medical device of claim 1, wherein the handle includes a first half portion and a second half portion positioned on opposite sides of a plane extending along a longitudinal axis of the handle, the first half portion and the second half portion being coupled together via a plurality of connectors.

6. The medical device of claim 1, wherein the tubing assembly includes a fitting adapted for attachment to a centralized gas supply.

7. A medical device for delivering a breast implant to a subject, comprising:
   a shaft extending between a proximal end and a distal end, the shaft including a lumen therein, the distal end of the shaft including a nozzle that comprises a polymer and defines a distal aperture, wherein the shaft is configured to compress the breast implant and has an inner diameter ranging from about 1-3 inches;

a handle detachably coupled to the shaft and including an actuator;
a valve mechanism disposed within the handle in communication with the actuator; and
a tubing assembly having a first end coupled to the handle and a second end adapted for attachment to a centralized gas supply, the tubing assembly including a pressure line extending through a body of the handle;
wherein the actuator is configured to engage the valve mechanism to control fluid flow to the shaft through the pressure line so as to impart a positive pressure in at least a portion of the lumen.

8. The medical device of claim 7, wherein the medical device is configured to compress the breast an implant to a profile diameter in the range of about 1.0 cm to about 3.0 cm for insertion into an incision.

9. The medical device of claim 7, the handle includes a first half portion and a second half portion positioned on opposite sides of a plane extending along a longitudinal axis of the handle, the first half portion and the second half portion being coupled together via a plurality of connectors.

10. The medical device of claim 7, wherein the tubing assembly includes a fitting adapted for attachment to a centralized gas supply.

11. The medical device of claim 7, wherein the nozzle is tapered.

* * * * *

UNITED STATES PATENT AND TRADEMARK OFFICE
CERTIFICATE OF CORRECTION

Page 1 of 1

PATENT NO. : 10,905,466 B2
APPLICATION NO. : 16/092878
DATED : February 2, 2021
INVENTOR(S) : Juan Jose Chacon Quiros et al.

It is certified that error appears in the above-identified patent and that said Letters Patent is hereby corrected as shown below:

In the Claims

Claim 1, Column 20, Lines 31-32, replace "to compress the implant has an inner diameter" with -- to compress the implant and has an inner diameter --.

Signed and Sealed this
Tenth Day of May, 2022

Katherine Kelly Vidal
*Director of the United States Patent and Trademark Office*